United States Patent
Jannicke et al.

(10) Patent No.: US 9,351,783 B2
(45) Date of Patent: May 31, 2016

(54) DIAGNOSTIC GUIDEWIRE FOR CRYOABLATION SENSING AND PRESSURE MONITORING

(71) Applicant: MEDTRONIC CRYOCATH LP, Toronto (CA)

(72) Inventors: Jeffrey J. Jannicke, Andover, MN (US); Mark Allen Benscoter, Dellwood, MN (US); Patricia K. Fuher, Brooklyn Park, MN (US)

(73) Assignee: Medtronic CryoCath LP, Toronto, Ontario (CA)

( * ) Notice: Subject to any disclaimer, the term of this patent is extended or adjusted under 35 U.S.C. 154(b) by 98 days.

(21) Appl. No.: 13/874,626

(22) Filed: May 1, 2013

(65) Prior Publication Data
US 2014/0330262 A1 Nov. 6, 2014

(51) Int. Cl.
*A61B 18/02* (2006.01)
*A61B 17/00* (2006.01)
(Continued)

(52) U.S. Cl.
CPC ........... *A61B 18/02* (2013.01); *A61B 2017/003* (2013.01); *A61B 2017/00053* (2013.01);
(Continued)

(58) Field of Classification Search
CPC .... A61B 18/02; A61B 18/0218; A61B 18/14; A61B 18/1492; A61B 2018/0212; A61B 2018/00577; A61B 2018/0262; A61B 2018/0022; A61B 2018/0293; A61B 2018/00351; A61B 2018/00642; A61B 2018/00214
USPC ...................................... 606/20–26
See application file for complete search history.

(56) References Cited

U.S. PATENT DOCUMENTS

| 5,549,109 | A | 8/1996 | Samson et al. |
| 5,673,695 | A | 10/1997 | McGee et al. |

(Continued)

FOREIGN PATENT DOCUMENTS

| EP | 2471455 A3 | 10/2012 |
| WO | 03003930 A1 | 1/2003 |
| WO | 2011037978 A3 | 3/2011 |

OTHER PUBLICATIONS

International Search Report and Written Opinion dated Jul. 11, 2014 for International Application Serial No. PCT/CA2014/000308, International Filing Date: Apr. 1, 2014 consisting of 16 pages.

(Continued)

*Primary Examiner* — Michael Peffley
*Assistant Examiner* — Khadijeh Vahdat
(74) *Attorney, Agent, or Firm* — Christopher & Weisberg, P.A.

(57) ABSTRACT

A method and system for performing pulmonary vein isolation, mapping, and assessing pulmonary vein occlusion using a single device. The device may generally include an ablation element, such as a cryoballoon, and a sensing component slidably disposed within a lumen of the device and bearing one or more mapping electrodes and one or more pressure sensors. The method may generally include mapping cardiac electrical signals within a heart and/or pulmonary vein, positioning a distal portion of the sensing component within a pulmonary vein, advancing the ablation element until it is in contact with the pulmonary vein ostium, recording blood pressure measurements within the pulmonary vein with the one or more pressure sensors to assess pulmonary vein occlusion, and activating the treatment element when the pulmonary vein is completely occluded. The sensing component may have a straight or hooped configuration, or a configuration therebetween.

9 Claims, 5 Drawing Sheets

(51) Int. Cl.
*A61B 18/00* (2006.01)
*A61B 19/00* (2006.01)

(52) U.S. Cl.
CPC ............... *A61B2018/0022* (2013.01); *A61B 2018/00351* (2013.01); *A61B 2018/00357* (2013.01); *A61B 2018/00839* (2013.01); *A61B 2018/0212* (2013.01); *A61B 2019/464* (2013.01); *A61B 2019/465* (2013.01)

(56) References Cited

U.S. PATENT DOCUMENTS

| | | | |
|---|---|---|---|
| 5,711,298 A | | 1/1998 | Littmann et al. |
| 5,716,389 A | | 2/1998 | Walinsky et al. |
| 5,957,842 A | | 9/1999 | Littmann et al. |
| 6,139,540 A | * | 10/2000 | Rost et al. .................. 600/585 |
| 7,101,368 B2 | * | 9/2006 | Lafontaine .................. 606/21 |
| 7,783,365 B2 | | 8/2010 | Ebert et al. |
| 7,881,806 B2 | | 2/2011 | Horrigan et al. |
| 7,962,208 B2 | | 6/2011 | Shuros et al. |
| 8,103,358 B2 | | 1/2012 | Sommer et al. |
| 8,209,032 B2 | | 6/2012 | Ebert et al. |
| 8,764,709 B2 | * | 7/2014 | Chang et al. ............. 604/164.01 |
| 8,821,484 B2 | * | 9/2014 | Ingle et al. .................. 606/21 |
| 2001/0007070 A1 | * | 7/2001 | Stewart ............. A61B 18/1492 606/41 |
| 2005/0215989 A1 | | 9/2005 | Abboud et al. |
| 2006/0135953 A1 | * | 6/2006 | Kania et al. .................. 606/21 |
| 2008/0243195 A1 | | 10/2008 | Sommer et al. |
| 2008/0243215 A1 | | 10/2008 | Sommer et al. |
| 2009/0112128 A1 | | 4/2009 | Schiff et al. |
| 2009/0299355 A1 | | 12/2009 | Bencini et al. |
| 2011/0071608 A1 | | 3/2011 | Fleischhacker et al. |
| 2012/0130220 A1 | * | 5/2012 | Maskara et al. ............. 600/374 |
| 2012/0232409 A1 | * | 9/2012 | Stahmann et al. ........... 600/483 |
| 2013/0169624 A1 | * | 7/2013 | Bourier et al. ............... 345/419 |
| 2013/0197497 A1 | | 8/2013 | Wittenberger et al. |

OTHER PUBLICATIONS

Siklódy, et al., Pressue-Guided Cryoballoon Isolation of the Pulmonary Veins for the Treatment of Proxysmal Atril Fibrillation, J Cardiovasc Electrophysiol, vol. 21, pp. 120-125, Feb. 2010.

\* cited by examiner

DIAGNOSTIC GUIDEWIRE FOR CRYOABLATION SENSING AND PRESSURE MONITORING

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for both ablating cardiac tissue using a treatment element and assessing the position of the treatment element within a portion of a patient's anatomy using a single device.

BACKGROUND OF THE INVENTION

A cardiac arrhythmia is a condition in which the heart's normal rhythm is disrupted. There are many types of cardiac arrhythmias, including supraventricular arrhythmias that begin above the ventricles (such as premature atrial contractions, atrial flutter, accessory pathway tachycardias, atrial fibrillation, and AV nodal reentrant tachycardia), ventricular arrhythmias that begin in the lower chambers of the heart (such as premature ventricular contractions, ventricular tachycardia, ventricular fibrillation, and long QT syndrome), and bradyarrhythmias that involve slow heart rhythms and may arise from disease in the heart's conduction system.

Certain types of cardiac arrhythmias, including ventricular tachycardia and atrial fibrillation, may be treated by ablation (for example, radiofrequency (RF) ablation, cryoablation, ultrasound ablation, laser ablation, microwave ablation, and the like), either endocardially or epicardially. For example, atrial fibrillation (AF) is frequently treated with pulmonary vein ablation (also called pulmonary vein antrum isolation, or PVAI), a procedure that may involve inserting a guide wire and then a mapping device into a pulmonary vein (PV) to map electrical impulses within the vein. Once the mapping catheter is properly seated within the PV, an ablation element (such as a cryoballoon or RF ablation device) is advanced over the mapping catheter until it is in contact with the ostium of the PV, within the left atrium. After ablation of the ostial tissue, the mapping catheter may then be used to confirm PV isolation. That is, the mapping catheter may be used to determine whether aberrant electrical conductivity is still present.

When a cryoballoon is used as the ablation element in a PVAI procedure, it is desirable that the cryoballoon is in complete contact with the PV ostial tissue so as to totally occlude the PV. Therefore, such a PVAI procedure may include a step between positioning the device at the PV ostium and activating the ablation element wherein contrast dye is injected from the device into the pulmonary vein to assess vein occlusion. Fluoroscopy may be used to visualize the contrast dye to determine whether any of the dye escapes from the pulmonary vein into the left atrium. For example, if the cryoballoon forms a tight seal against the ostium, no dye will be able to escape into the left atrium. If the cryoballoon is not properly seated, on the other hand, fluoroscopy may show the presence of contrast dye in the left atrium.

Although the use of contrast is effective and generally safe, it is desirable to introduce as few components, including chemicals, into a patient as possible. Further, the use of contrast dye necessitates the extra step of fluoroscopic visualization, which can be time consuming and requires additional equipment.

It is desirable, therefore, to provide a system that combines mapping and occlusion verification capabilities with an ablation device to provide real-time physiological data and to simplify a PVAI procedure.

SUMMARY OF THE INVENTION

The present invention advantageously provides a method and system for assessing the position of the treatment element within a portion of a patient's anatomy using a diagnostic guidewire (also referred to herein as a "sensing component"). The system may generally include a medical device including an elongate body defining a distal portion, a proximal portion, and a lumen therebetween, a treatment element coupled to the distal portion of the elongate body, and a sensing component slidably disposed within the elongate body lumen, the sensing component having one or more mapping elements and a pressure sensor. The system may further include a console including a processor in communication with the treatment element and sensing component, the pressure sensor transmitting blood pressure measurements to the processor, the processor assessing the position of the medical device based at least in part on the blood pressure measurements. The treatment element may be an expandable element, such as a cryoballoon that is fluid communication with a coolant reservoir located within the console. The sensing component may define a distal portion having a distal tip, the one or more mapping elements being disposed on the distal portion of the sensing component. The pressure sensor may be disposed on the distal tip of the sensing component, and may be located distal of the treatment element when the medical device is in use. The sensing component may define a central lumen, the medical device further including a push rod slidably disposed within the central lumen of the sensing component, the push rod defining a proximal portion and a distal portion. Further, the distal portion of the sensing component may be transitionable between a first configuration (such as a curved or hooped configuration) and a second configuration (such as a straight or substantially linear configuration) using a steering mechanism coupled to the proximal portion of the push rod. The distal tip may have a J-shape wherein the distal tip on which the pressure sensor is disposed is oriented toward the treatment element.

In one embodiment, the method may include providing a medical device including a treatment element (such as a cryoballoon) and a sensing component having a pressure sensor, positioning the treatment element in contact with cardiac tissue, recording a blood pressure measurement within a pulmonary vein using the pressure sensor, and assessing the position of the treatment element based on the blood pressure measurement. The medical device may further include an elongate body defining a distal portion, a proximal portion, and a lumen therebetween, the treatment element being coupled to the distal portion of the elongate body and the sensing component being slidably disposed within the elongate body lumen, the sensing component further having one or more mapping elements. The medical device may further include a handle having a steering mechanism and a push rod defining a proximal portion and a distal portion, the sensing component having a proximal portion, a distal portion, and a central lumen therethrough, the push rod being slidably disposed within the central lumen, the proximal portion of the push rod being coupled to steering mechanism. For example, actuating the steering mechanism in a first direction may advance the push rod a distance within the sensing component central lumen to cause the distal portion of the sensing component to transition to a first configuration, and actuating the steering mechanism in a second direction may retract the push rod a distance within the sensing component central lumen to cause the distal portion of the sensing component to transition to a second configuration. The method may further include providing a console including a processor in communication with the one or more mapping elements and the pressure sensor. The method may further include recording an initial blood pressure measurement before positioning the treatment element in contact with cardiac tissue and comparing the initial blood pressure measurement to the blood pressure measurement after positioning the treatment element in contact with cardiac tissue. The pressure sensor may transmit blood pressure measurements to the processor, the processor using the blood pressure measurements to determine a first position of the treatment element when the blood pressure measurements are within a first range and to determine a second position of the treatment element when the blood pressure measurements are within a second range, the second range being higher than the first range. For example, the treatment element may completely occlude a pulmonary vein when in the first position, and the treatment element may partially occlude a pulmonary vein when the in the second position.

In another embodiment, the method may generally include providing a medical system including a cryoballoon and a sensing component, the sensing component including a distal portion on which one or more mapping elements and a pressure sensor are disposed, positioning at least a portion of the distal portion of the sensing component within a pulmonary vein, recording electrical signals generated by pulmonary vein tissue using the one or more mapping elements and recording a first set of blood pressure measurements within the pulmonary vein using the pressure sensor, positioning the cryoballoon in contact with at least a portion of an ostium of the pulmonary vein in which the at least a portion of the distal portion of the sensing component is positioned, recording a second set of blood pressure measurement within the pulmonary vein using the pressure sensor, transmitting the blood pressure measurement to a processor, the processor assessing occlusion of the pulmonary vein by the cryoballoon based on the blood pressure measurement, and repositioning the cryoballoon if the processor determines that the pulmonary vein is not completely occluded. The processor may assess occlusion of the pulmonary vein based at least in part on a comparison between the first set of blood pressure measurements and the second set of blood pressure measurements.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
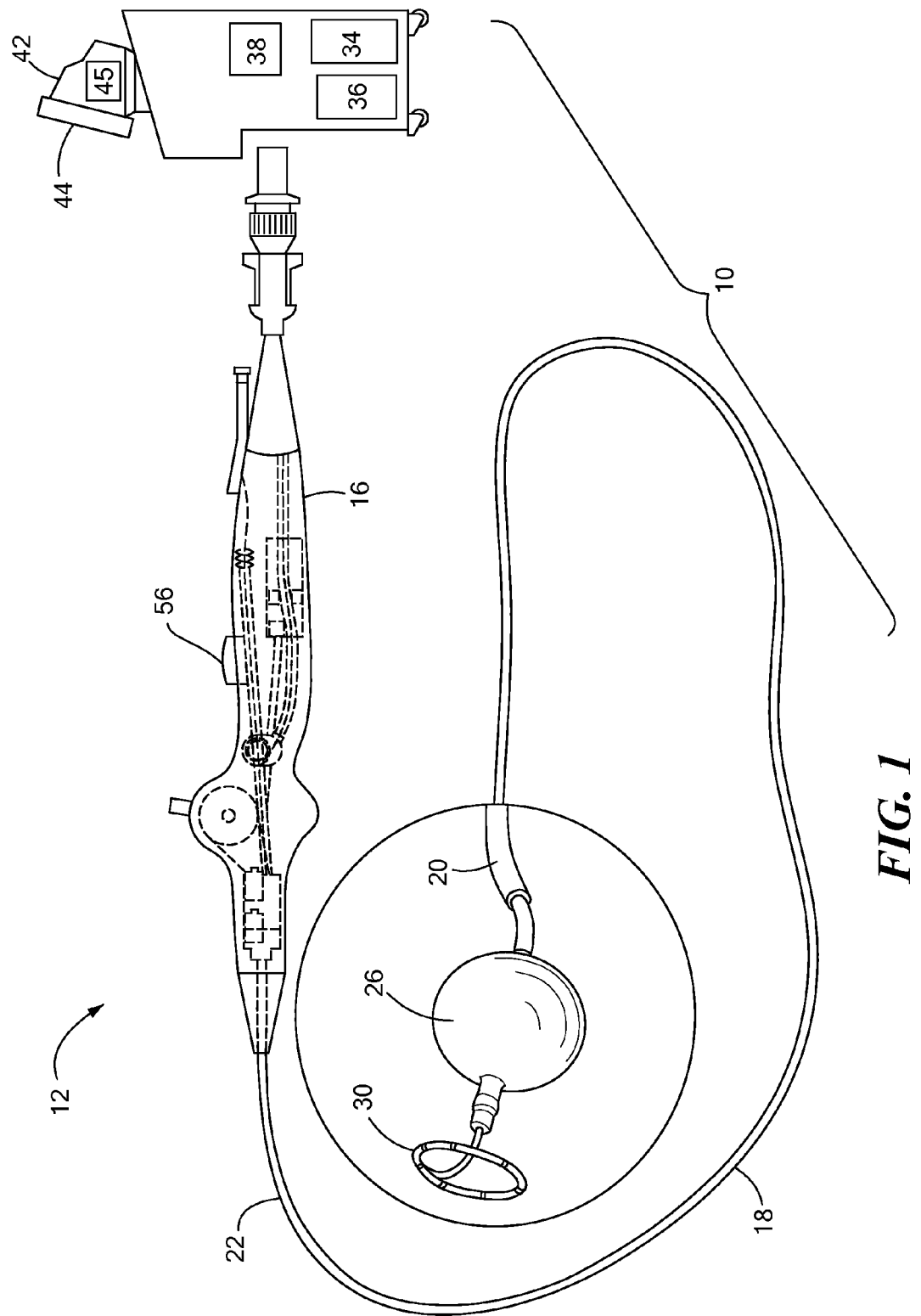
FIG. 1 shows a system including an medical device having a treatment element and a sensing component.

Referring now to FIG. 1, a system including a medical device having an ablation element and a sensing component is shown. The system 10 may generally include a medical device 12 for mapping and treating an area of tissue and detecting a pressure value proximate the device, and a console 14 that houses various system 10 controls. The system 10 may be adapted for cryoablation. The system 10 may additionally be adapted for radiofrequency (RF) ablation and/or phased RF ablation, ultrasound ablation, laser ablation, microwave ablation, hot balloon ablation, or other ablation methods or combinations thereof.

Figure 3:
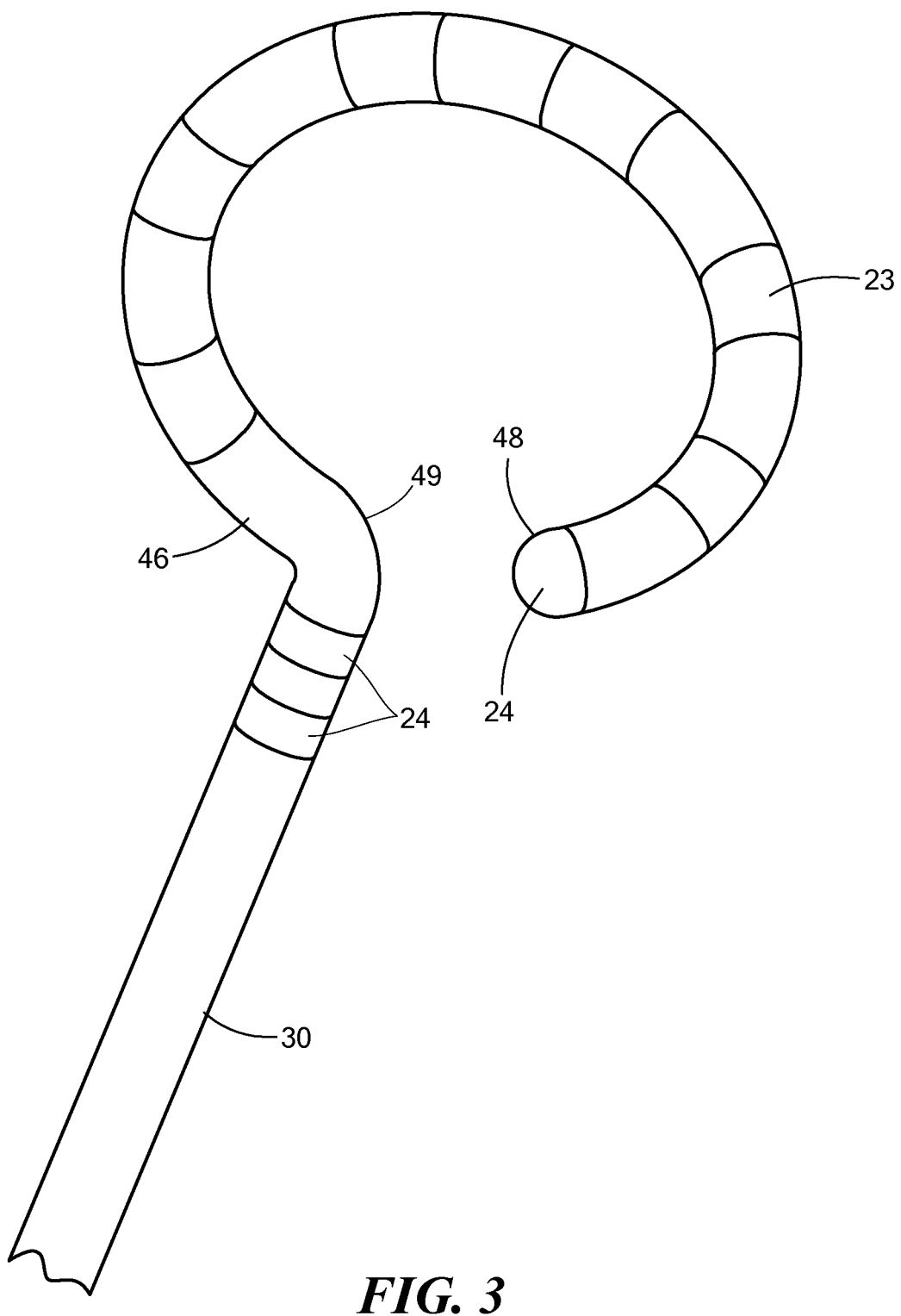
FIG. 3 shows a distal portion of a sensing component in a hooped configuration.
Figure 4:
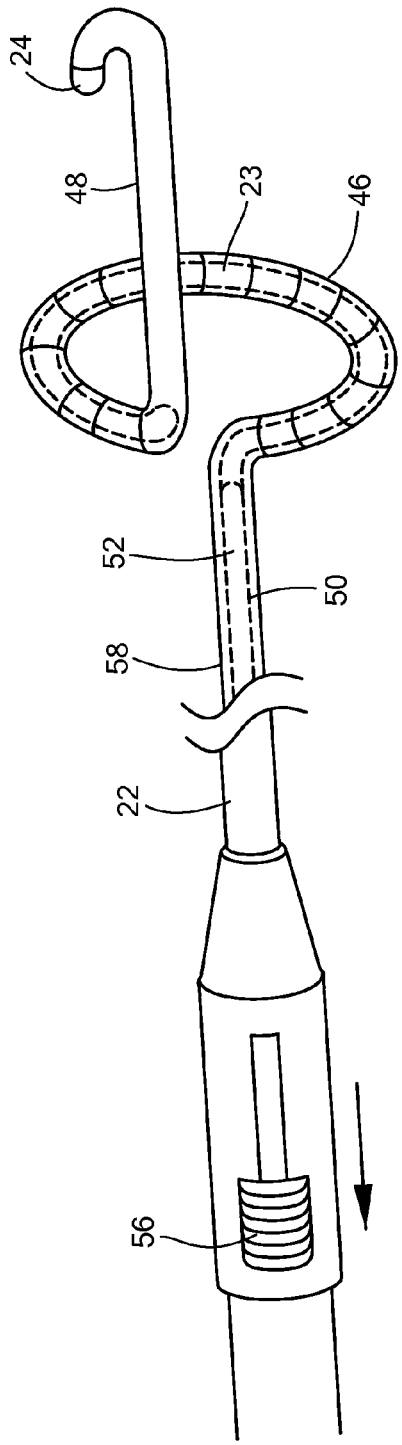
FIG. 4 shows a sensing component in a hooped configuration with a J-shaped tip.

The device 12 may be a catheter with mapping, pressure detection, and treatment functionality that generally includes a handle 16, an elongate body 18 having a distal portion 20 and a proximal portion 22, one or more mapping elements 23, one or more sensors 24, and one or more treatment elements 26. The device 12 may have a longitudinal axis 28. The device 12 may include two or more components. For example, the device 12 may include a treatment component that includes the one or more treatment elements 26, such as a cryoballoon (as shown in FIG. 1). The treatment component may be integrated with or coupled to the elongate body 18 of the device 12. As a further example, the device 12 may also include a sensing component (also referred to herein as the "diagnostic guidewire") 30 that includes the one or more mapping elements 23 and the one or more sensors 24 (as shown in FIGS. 2-4).

The elongate body 18 of the device 12 may include one or more lumens. As shown in FIG. 1, the treatment component of the device 12 may include a guidewire lumen 32 in which the sensing component 30 is slidably disposed. Further, if the device 12 is a cryoablation catheter, for example, the elongate body 18 may include a main lumen, a fluid injection lumen in fluid communication with the coolant reservoir 34, and a fluid return lumen in fluid communication with the coolant return reservoir 36. Depending on the energy modality being used, the lumens of the elongate body 18 may be in fluid communication with any of a number of fluids, such as saline. In some embodiments, one or more other lumens may be disposed within the main lumen, and/or the main lumen may function as the fluid injection lumen or the fluid return lumen. If the ablation catheter includes thermoelectric cooling elements or electrodes capable of transmitting radiofrequency (RF), ultrasound, microwave, electroporation energy, or the like, the elongate body 18 may include a lumen in electrical communication with an energy generator 38.

The console 14 may be in electrical and fluid communication with the medical device 12 and include one or more fluid (such as coolant or saline) reservoirs 34, fluid return reservoirs 36, energy generators 38 (for example, an RF or electroporation energy generator), and computers 42 with displays 44, and may further include various other displays, screens, user input controls, keyboards, buttons, valves, conduits, connectors, power sources, processors, and computers for adjusting and monitoring system 10 parameters. The computer 42 may include one or more processors 45 that are in electrical communication with the one or more mapping elements 23, the one or more sensors 24, and the one or more treatment elements 26 and programmable to execute an algorithm for locating one or more optimal treatment areas.

Figure 2:
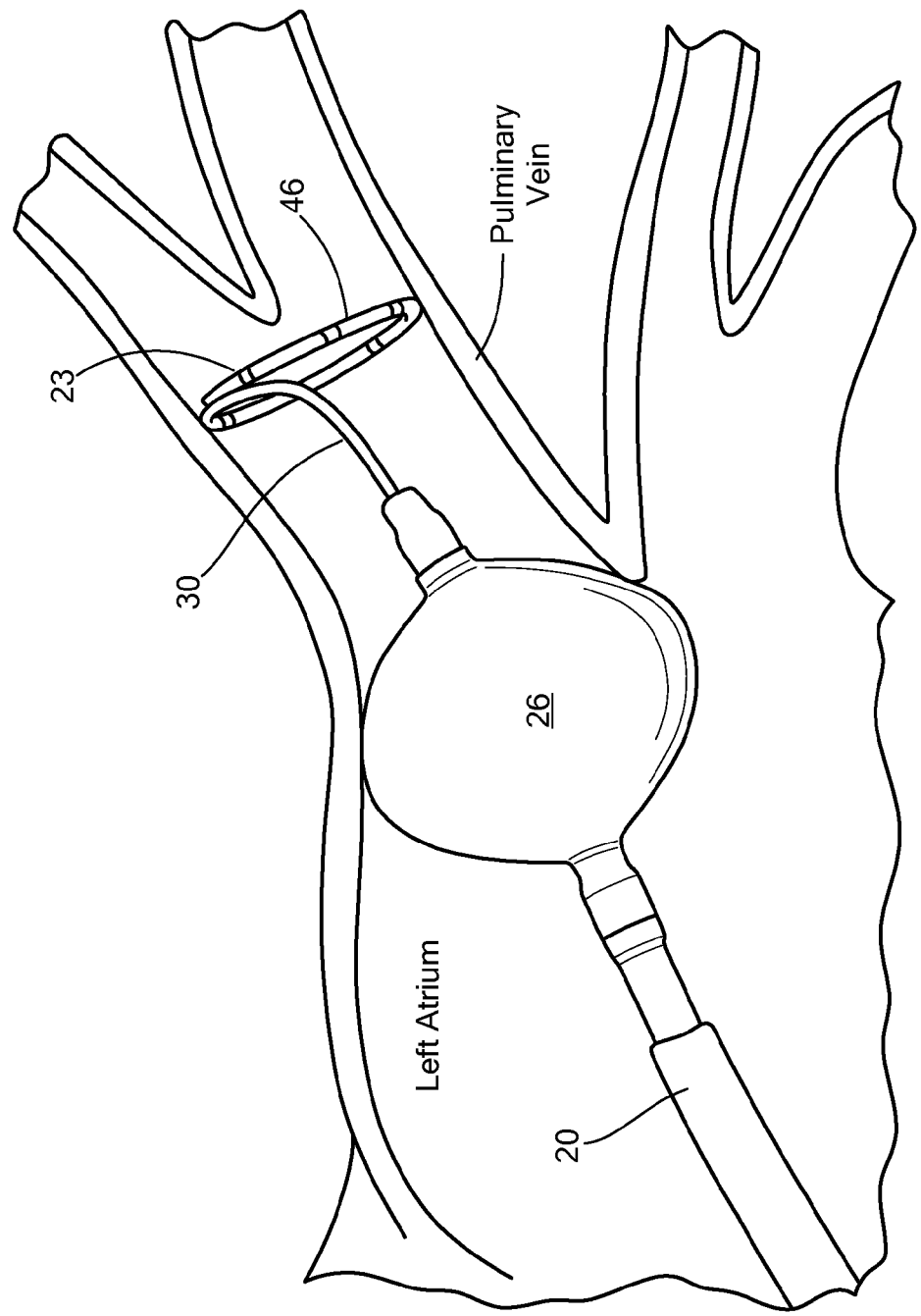
FIG. 2 shows a medical device with a sensing element disposed within a pulmonary vein and a treatment element positioned against the pulmonary vein ostium.

Referring now to FIG. 2, a medical device is shown with a sensing element disposed within a pulmonary vein and a treatment element positioned against the pulmonary vein ostium. As shown and described in more detail in FIGS. 3-6, the medical device of FIG. 1 may be positioned within the patient's anatomy such that at least a portion of the sensing element 30 is located within a pulmonary vein. For example, the distal portion 46 of the sensing component 30 may have a hooped configuration (as shown in FIGS. 2-4), which may be positioned within a pulmonary vein for mapping pulmonary vein tissue and sensing blood pressure within the pulmonary vein distal of the treatment element 26. The treatment element 26, such as a cryoballoon, may be in contact with the ostium of the pulmonary vein. Ideally, the treatment element 26 will completely occlude the pulmonary vein so that blood is prevented from exiting the pulmonary vein into the left atrium of the patient's heart. Occlusion may be assessed using blood pressure measurements recorded by the one or more sensors 24, such as a pressure sensor.

Referring now to FIG. 3, a distal portion of a sensing component (or diagnostic guidewire) in a hooped configuration is shown. The sensing component 30 may be circular in cross section, and may have a diameter between approximately 0.030 inch and approximately 0.039 inch. As shown and described in FIG. 1, the distal portion 46 of the sensing component 30 may include one or more mapping elements 23 and one or more sensors 24. The mapping elements 23 may be sensors or electrodes capable of sensing electrical activity within the myocardial cells as the cells polarize and depolarize, such as electrogram mapping electrodes. Further, the one or more mapping elements 23 may be used for cardiac stimulation during electrophysiology studies. The mapping elements 23 may be electrodes that are coupled to or disposed on at least a portion of the sensing component 30 (for example, the mapping elements 23 may be band electrodes that are disposed about the outer circumference of the sensing component 30) or the mapping elements 23 may be exposed conductive portions of the sensing component 30. For example, the sensing component 30 may be composed of an electrically conductive material covered with an insulative layer (for example, a layer of tantalum oxide). One or more areas of the electrically conductive material may be exposed or not covered with the insulative layer, and these areas may serve as mapping elements 23. Although the one or more mapping elements 23 are capable of sensing electrical signals, they may be distinguished from the one or more sensors 24 in that the one or more sensors 24 are capable of detecting non-electrical signals, such as pressure, pH, temperature, or the like. For example, the sensing component of FIGS. 2-5 may include a pressure sensor 24 that records blood pressure measurements in locations such as within a pulmonary vein. For example, when a treatment element 26 such as a cryoballoon is positioned such that it completely occludes the ostium of a pulmonary vein, oxygenated blood from the lungs traveling through the pulmonary vein is prevented from flowing into the left atrium of the heart by the cryoballoon 26. As a result, blood pools within the pulmonary vein distal of the cryoballoon 26 and surrounding the sensing component 30, and the pressure sensor 24 will record a higher pressure measurement than if the pulmonary vein were not occluded or were only partially occluded and blood were allowed to flow into the heart. This pressure measurement may be communicated by the pressure sensor 24 to one or more processors within the console, where the measurements may then be used to assess the quality of contact between the pulmonary vein ostium and the cryoballoon 26. That is, pressure measurements recorded by the pressure sensor 24 may be used to determine whether the cryoballoon 26 is completely occluding the pulmonary vein. For example, a baseline pressure measurement may be recorded by the pressure sensor 24 within the pulmonary vein before the cryoballoon 26 is placed in contact with ostial or other cardiac tissue. Once the cryoballoon 26 is in position at the pulmonary vein ostium, the pressure sensor 24 may record a pressure measurement within a first blood pressure range if the pulmonary vein is not completely occluded, and may record a pressure measurement within a second blood pressure range if the pulmonary vein is completely occluded. The first pressure range is less than the second pressure range, as measured, for example, in millimeter of mercury (mmHg). Blood pressure measurements taken after the treatment element 26 is positioned in contact with the pulmonary vein ostium may be compared to blood pressure measurements taken before the treatment element 26 is positioned in contact with the pulmonary vein ostium (that is, before the pulmonary vein is partially or completely occluded). As a non-limiting example, a blood pressure measurement that is approximately 20 mmHg or more higher than the baseline blood pressure measurement (that is, an increase of at least approximately 20 mmHg) may be indicative of complete occlusion. Conversely, a blood pressure measurement that is less than 20 mmHg below the baseline blood pressure measurement (that is, an increase of less than approximately 20 mmHg) may be indicative of partial occlusion. When partial occlusion is indicated, the cryoballoon 26 may be repositioned and the measurements retaken.

Figure 5:
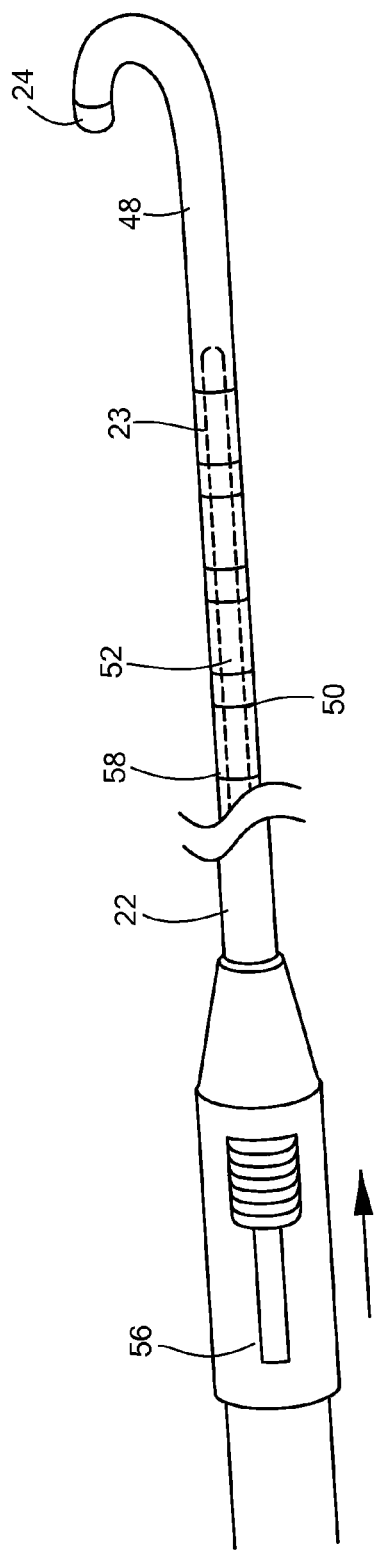
FIG. 5 shows a sensing component in a straight configuration with a J-shaped tip.

The sensing component 30 may be steerable and/or positionable in a variety of configurations (for example, as shown in FIGS. 2-5). As a non-limiting example, the distal portion 46 of the sensing component 30 may have a hooped configuration, as shown in FIGS. 2 and 3, or a hooped configuration with a J-shaped tip, as shown in FIG. 4. A hooped portion of the sensing component 30 may lie in a plane that is substantially orthogonal to the longitudinal axis 28 of the device 12. In this configuration, the hooped shape may be sized and positioned to be in contact with at least a portion of the inner circumference of a pulmonary vein, or to be in contact with a portion of the wall of the left atrium surrounding a pulmonary vein (for example, the pulmonary vein antrum), thus positioning the one or more mapping elements 23 to record electrical signals from the cardiac and/or pulmonary vein tissues. In a non-limiting example, the portion of the hooped shape bearing mapping elements 23 may be in contact with an entire circumferential portion of the pulmonary vein (that is, the hoop may define a complete 360-degree circle). Further, a pressure sensor 24 may be located on the distal tip 48 of the sensing component 30, and the distal tip 48 may be angled or positioned away from the inner circumference of, and toward the interior space of, the pulmonary vein (for example, as shown in FIG. 3). Alternatively, the distal tip may be a J-shaped tip (as shown in FIGS. 4-5). Alternatively still, one or more pressure sensors 24 may be disposed on the sensing component distal of the treatment element 26 and proximal of the one or more mapping elements, for example, just proximal of the initial bend 49 of the hooped structure (as shown in FIG. 3). Any of these positions may allow the one or more pressure sensors 24 to record pressure measurements from surrounding blood proximate a treatment element 26, which, in turn, may allow more precise measurements and more accurate real-time feedback about the procedure. Additionally, when the sensing component 30 is used within, for example, the left atrium of the heart, the pressure sensor 24 may be used to record blood pressure measurements within the heart. It will be understood that although FIG. 3 shows both a pressure sensor 24 at the distal tip 48 of the sensing component 30 and a plurality of pressure sensors 24 on the sensing component 30 proximal of the bend 49 of the hooped structure, the sensing component 30 may include any number and/or configuration of sensors 24, including pressure sensors. For example, the sensing component 30 may only include a single pressure sensor 24 at the distal tip 48, as shown in FIGS. 4 and 5.

Referring now to FIGS. 4 and 5, the sensing component or diagnostic guidewire 30 may include one or more mapping elements 23 on the distal portion 46 of the sensing component 30 and a pressure sensor 24 at the distal tip 48 of the sensing component 30. The one or more mapping elements 23 and pressure sensor 24 may be as shown and described in, for example, FIG. 3. Unlike the sensing component distal portion 46 shown in FIG. 3, the distal portion 46 of the sensing component 30 shown in FIGS. 4 and 5 includes a J-shaped distal tip 48. Referring now to FIG. 4, a distal portion of a sensing component (or diagnostic guidewire) in a hooped configuration with a J-shaped tip is shown. The configuration shown in FIG. 4 may allow the one or more mapping elements 23 to be in contact with at least a portion of the inner circumference of the pulmonary vein. As a non-limiting example, the distal portion 46 of the sensing component 30 may be naturally biased toward the hooped configuration shown in FIG. 4. The distal tip 48 of the sensing component 30 may be "floppier" than the rest of the distal portion 46 of the sensing component 30. For example, the distal tip 48 may be composed of a material with a lower durometer than the rest of the distal portion 46 proximal to the distal tip or may have a smaller diameter than the rest of the distal portion 46. As a result, the distal tip 48 may be sufficiently flexible to be inserted into pulmonary veins with irregular geometries (for example, pulmonary veins with an inner circumference that is not perfectly round) without catching, bunching, or injuring the patient. As a non-limiting example, the distal tip 48 may extend proximally from the distalmost point of the sensing component 30 for a distance of between approximately 3 mm and approximately 4 mm. Further, the distal tip 48 may be naturally biased toward the J-shape shown in FIGS. 4 and 5. The J-shaped tip of the sensing component 30 may enable the pressure sensor 24 to be oriented toward the cryoballoon 26, thus enhancing the quality and accuracy of the pressure measurements.

The sensing component 30 may include a central lumen 50 within which a push rod 52 may be slidably disposed. The lumen 50 may be coaxial with the device longitudinal axis 28, and the push rod 52 may be slidable along the common axis. To transition between the hooped configuration shown in FIG. 4 and the straight configuration shown in FIG. 5, the push rod 52 may be advanced through the lumen 50 toward the distal tip 48 of the sensing component 30. The lumen 50 may extend from the proximal portion 22 of the elongate body 18 to the distal portion 20 of the elongate body 18, proximate the distalmost mapping electrode 23 (for example, as shown in FIGS. 4 and 5). Thus, the push rod 52 will not straighten or interfere with the distal tip 48 of the sensing component 30, even when advanced to the end of the lumen 50. A proximal portion 54 of the push rod 52 may be in mechanical communication with a steering mechanism, such as the slider 56 shown in FIGS. 4 and 5. The slider 56 may be used to transition the distal end 46 of the sensing element 30 between a first configuration (such as the straight configuration shown in FIG. 4) and a second configuration (such as the hooped configuration shown in FIG. 5). For example, when the slider is in a first position, the distal end 46 of the sensing element 30 may be in the first configuration (as shown in FIG. 4). Likewise, positioning the slider 56 is in a second position may advance the push rod 52 through the lumen 50, thus causing the distal end 46 of the sensing element 30 to transition to the second configuration (as shown in FIG. 5). A steering mechanism such as a slider 54 may be integrated with or coupled to the handle 16 of the device 12 or a proximal portion 58 of the sensing component 30. As a non-limiting example, a slider 56 may be coupled to the proximal portion 58 of the sensing component 30, the proximal portion 58 being positioned extracorporally and outside of the handle 16 so the slider 56 is accessible to the user.

Figure 6:
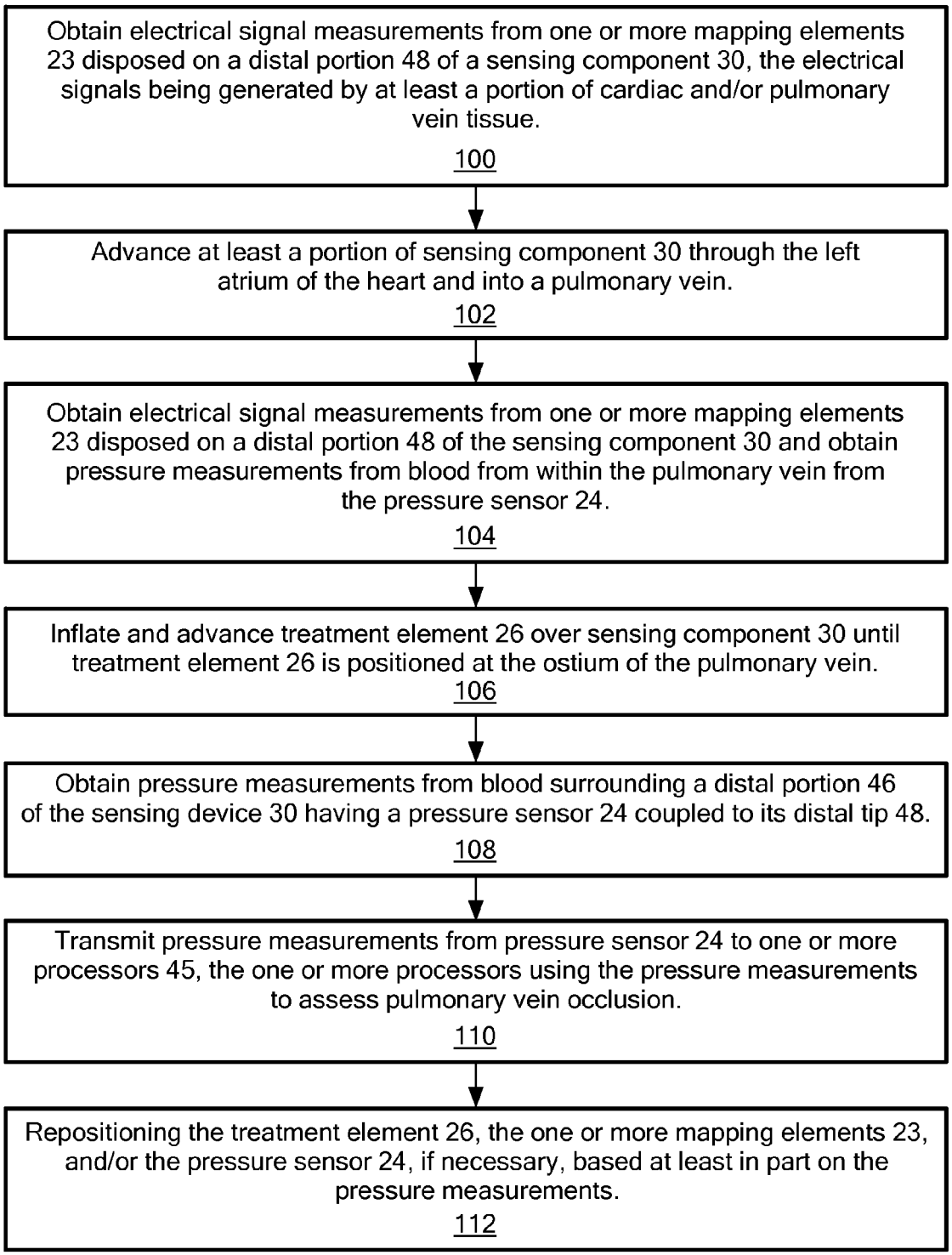
FIG. 6 shows a flow chart of an exemplary method of use of a system including a medical device having an ablation element and a sensing component.

Referring now to FIG. 6, a flow chart of an exemplary method of use of a system including a medical device having an ablation element and a sensing component is shown. As a non-limiting example, in the first step 100 of the method, the sensing component 30 may be configured in a straight configuration, a hooped configuration, or transitional configuration therebetween, and used to map (sense electrical activity within cardiac tissue) a portion of the patient's heart, pulmonary vein, and/or pulmonary vein ostium. When the sensing component 30 is in a straight configuration, the sensing component 30 will map a linear portion of tissue. Likewise, when the sensing component 30 is in a hooped configuration, the sensing component 30 will map a circular, semicircular, circumferential, or partially circumferential portion of tissue. In the second step 102 of the method, the sensing component 30 may be advanced through the left atrium of the patient's heart and into a pulmonary vein. Although not shown in the method flow chart of FIG. 6, a sheath may first be advanced through the patient's vasculature (such as by femoral, radial, or brachial access) and into the right atrium of the heart. A transseptal device may be advanced through the sheath to the septum, where it may be used to create a transseptal puncture. The transseptal device may then be withdrawn from the patients body, and the medical device 12 described herein may be advanced through the sheath and then through the transseptal puncture and into the left atrium of the heart. The treatment element 26 may be a cryoballoon that is delivered to the left atrium in a deflated state.

In the third step 104 of the method, the sensing component 30 may be advanced through the left atrium and into a pulmonary vein. Because the sensing component 30 may have a relatively small diameter and may be easily steerable, the distal portion 46 of the sensing component 30 may be easily positioned deep within a pulmonary vein. As a non-limiting example, the distal portion 46 of the sensing component 30 may be in a straight configuration when inserted into the pulmonary vein. Once within the pulmonary vein, the sensing component 30 may be transitioned from a straight configuration to a hooped configuration, or configuration between the straight and hooped configurations, such as by using a steering actuator such as the slider 56 to advance or retract the push rod 52. Alternatively, the sensing component 30 may be transitioned to a hooped configuration before entering the pulmonary vein. In fact, the distal portion 46 of the sensing component 30 may be adjusted to have any configuration, either within the pulmonary vein or the left atrium, suitable for the patient's anatomy and/or treatment being performed. For example, the distal portion 46 of the sensing component 30 may be placed inside the pulmonary vein and transitioned to the hooped configuration. This configuration may help to stabilize the sensing component 30 within the pulmonary vein, and may create contact between the pulmonary vein tissue and the one or more mapping elements 23 in order to record electrical signals from the tissue (third step 104 of the method). Further, preliminary blood pressure measurements may be recorded by the pressure sensor 24 to establish a baseline blood pressure value for an unoccluded pulmonary vein (that is, before the treatment element 26 partially or completely occludes the pulmonary vein).

In the fourth step 106 of the method, once the sensing component 30 is in place, the treatment element or cryoballoon 26 may be advanced over the sensing component 30 until the treatment element 26 is positioned within the left atrium, where the treatment element 26 may then be inflated. The inflated treatment element 26 may then be advanced over the sensing component 30 until the treatment element 26 is in contact with the ostium of the pulmonary vein. In this position, the treatment element 26 is positioned proximal of the distal portion 46 of the sensing component 30, which is positioned within the pulmonary vein. In the fifth and sixth steps 108, 110 of the method, pressure measurements from the blood surrounding the distal portion 46 of the sensing device may be recorded by the pressure sensor 24 and transmitted from the pressure sensor 24 to one or more processors 45 within the console 14. The one or more processors 45 may use the pressure measurements to assess pulmonary vein occlusion by the treatment element 26. For example, a blood pressure measurement within a first range and/or within a first percentage difference from the baseline blood pressure value may be indicative of partial occlusion of the pulmonary vein, whereas a blood pressure measurement within a second range and/or within a second percentage difference from the baseline blood pressure value may be indicative of complete occlusion of the pulmonary vein. The first pressure range and/or percentage difference is less than the second pressure range, as measured, for example, in millimeter of mercury (mmHg). This is because both complete and partial occlusion of the pulmonary vein will result in the buildup of blood in the pulmonary vein surrounding the distal portion 46 of the sensing element 30, but complete occlusion will result in greater blood buildup and therefore a greater measured blood pressure. The one or more processors 45 may compare the blood pressure measurements to the baseline blood pressure value to determine a value (or percentage) of change, and thus to determine whether the pulmonary vein is partially or completely occluded. Finally, in the seventh step 112 of the method, the treatment element 26, the one or more mapping elements 23, and/or the pressure sensor 24 may be repositioned if necessary, the determination based at least in part on the pressure measurements recorded by the pressure sensor 24. In this way, the position of the device 12 in general, and the ablation element 26 in particular, may be assessed based at least in part on blood pressure measurements recorded by the pressure sensor 24. Once it is determined that the treatment element 26 is completely occluding the pulmonary vein, the treatment element 26 may be activated to cool or ablate the tissue of the ostium, such as by the injection of coolant from the coolant reservoir 34 into the treatment element 26.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of occluding a pulmonary vein within a patient's body, the method comprising:
   providing a medical device including a treatment element, a longitudinal axis, and an elongate body defining a distal portion, a proximal portion, and a lumen therebetween, the treatment element being coupled to the distal portion of the elongate body;
   providing a sensing component having a pressure sensor and one or more mapping elements, the sensing component being longitudinally movable within the elongate body lumen, the sensing component having a hooped portion that is substantially orthogonal to the longitudinal axis of the medical device and a distal tip portion having a J-shape, the J-shaped distal portion including a linear portion located distal to the hooped portion and lying along an axis that is parallel to the longitudinal axis of the elongate body;
   providing a console processor in communication with the one or more mapping elements and the pressure sensor;
   recording a first blood pressure measurement within the pulmonary vein with the pressure sensor, the pressure sensor transmitting the first blood pressure measurement to the console processor;
   then positioning the treatment element in contact with a cardiac tissue and positioning a distal portion of the sensing component within the pulmonary vein;
   then recording a second blood pressure measurement within the pulmonary vein using the pressure sensor after positioning the treatment element in contact with the cardiac tissue, the pressure sensor transmitting the second blood pressure measurement to the console processor;
   comparing the first blood pressure measurement to the second blood pressure measurement, the console processor using the first blood pressure measurement and the second blood pressure measurements to determine substantial occlusion of the pulmonary vein by the treatment element when the second blood pressure measurement is within a first range and to determine partial occlusion of the pulmonary vein by the treatment element when the second blood pressure measurement is within a second range, the first range being higher than the second range.

2. The method of claim 1, wherein the pressure sensor is oriented toward the treatment element.

3. The method of claim 1, wherein the second blood pressure measurement when within the first range is at least approximately 20 mmHg higher than the initial blood pressure measurement.

4. The method of claim 1, the medical device further including a handle having a steering mechanism and a push rod defining a proximal portion and a distal portion, the sensing component having a proximal portion, a distal portion, and a central lumen therethrough, the push rod being slidably disposed within the central lumen with the proximal portion of the push rod being coupled to the steering mechanism.

5. The method of claim 4, wherein actuating the steering mechanism in a first direction advances the push rod a distance within the sensing component central lumen to cause the distal portion of the sensing component to transition to a first configuration, and actuating the steering mechanism in a second direction retracts the push rod a distance within the sensing component central lumen to cause the distal portion of the sensing component to transition to a second configuration.

6. The method of claim 5, wherein the first configuration is a substantially linear configuration and the second configuration is a curved configuration.

7. The method of claim 1, wherein the treatment element is a cryoballoon in fluid communication with a coolant reservoir.

8. A method for ablating cardiac tissue, the method comprising:
providing a medical system including a cryoballoon and a sensing component, the sensing component being longitudinally movable through the cryoballoon and including a distal portion on which one or more mapping elements and a pressure sensor are disposed;
positioning at least a portion of the distal portion of the sensing component within a pulmonary vein;
recording electrical signals generated by pulmonary vein tissue using the one or more mapping elements and recording a first set of blood pressure measurements within the pulmonary vein using the pressure sensor;
then positioning the cryoballoon in contact with at least a portion of an ostium of the pulmonary vein in which the at least a portion of the distal portion of the sensing component is positioned;
recording a second set of blood pressure measurements within the pulmonary vein using the pressure sensor;
transmitting the first and second set of blood pressure measurements to a processor, the processor assessing occlusion of the pulmonary vein by the cryoballoon based on a comparison between the first and second set of blood pressure measurements;
repositioning the cryoballoon if the processor determines that the pulmonary vein is not completely occluded; and
activating the cryoballoon to ablate at least a portion of the ostium of the pulmonary vein.

9. The method of claim 8, wherein the processor determines that the pulmonary vein is substantially occluded when the second set of blood pressure measurements are at least approximately 20 mmHg greater than the first set of blood pressure measurements.

* * * * *